United States Patent
Yan et al.

(10) Patent No.: US 10,502,681 B2
(45) Date of Patent: Dec. 10, 2019

(54) APPARATUS AND METHOD FOR MEASURING CONCENTRATION OF POLLUTANTS IN WATER

(71) Applicant: SHENZHEN UNIVERSITY, Shenzhen (CN)

(72) Inventors: Peiguang Yan, Shenzhen (CN); Hao Chen, Shenzhen (CN); Fengfei Xing, Shenzhen (CN); Min Zhang, Shenzhen (CN)

(*) Notice: Subject to any disclaimer, the term of this patent is extended or adjusted under 35 U.S.C. 154(b) by 0 days.

(21) Appl. No.: 16/353,084

(22) Filed: Mar. 14, 2019

(65) Prior Publication Data
US 2019/0204213 A1 Jul. 4, 2019

Related U.S. Application Data

(63) Continuation of application No. PCT/CN2016/112386, filed on Dec. 27, 2016.

(51) Int. Cl.
*G01N 21/31* (2006.01)
*H01S 3/115* (2006.01)
(Continued)

(52) U.S. Cl.
CPC .......... *G01N 21/31* (2013.01); *G02B 6/021* (2013.01); *G02F 1/35* (2013.01);
(Continued)

(58) Field of Classification Search
CPC .... G01N 21/31; G01N 21/35; G01N 21/3504; G01N 2201/088; G01N 33/1826;
(Continued)

(56) References Cited

U.S. PATENT DOCUMENTS

2009/0219955 A1 9/2009 Kakui
2016/0099541 A1 4/2016 Xu et al.

FOREIGN PATENT DOCUMENTS

CN 1793849 A 6/2006
CN 1793850 A 6/2006
(Continued)

OTHER PUBLICATIONS

Gangopadhyay et al. "Detection of chemicals using a novel fiber-optic sensor element built in fiber loop ring-resonators", ElsevierB. V.,Sensors and Actuators B, vol. 206, Jan. 2015, pp. 327-335. (Year: 2015).*

(Continued)

*Primary Examiner* — Michael P Mooney
(74) *Attorney, Agent, or Firm* — W&K IP

(57) ABSTRACT

The present disclosure provides an apparatus and a method for measuring a concentration of pollutants in water. A passive Q-switched fiber laser outputs an evanescent wave to a to-be-tested water sample after emitting a Q-switched pulse laser signal and transmitting it via an evanescent field fiber, and based on an evanescent wave change caused by an absorption effect of the pollutants in the to-be-tested water sample to the evanescent wave and an output repetition frequency change of the passive Q-switched fiber laser due to the evanescent wave change, outputs an output repetition frequency result of the passive Q-switched fiber laser. The method is simple; and the apparatus based on the method is simple in structure and low in cost.

6 Claims, 3 Drawing Sheets

(51) Int. Cl.
- *H01S 3/102* (2006.01)
- *H01S 3/094* (2006.01)
- *G02B 6/02* (2006.01)
- *G02F 1/35* (2006.01)
- *H01S 3/067* (2006.01)
- *G01N 33/18* (2006.01)

(52) U.S. Cl.
CPC ...... *H01S 3/094003* (2013.01); *H01S 3/1028* (2013.01); *H01S 3/115* (2013.01); *G01N 33/1826* (2013.01); *H01S 3/06791* (2013.01)

(58) Field of Classification Search
CPC ... G02B 6/00; G02B 6/02; G02B 6/10; G02B 6/021; H01S 3/094003; H01S 3/1028; H01S 3/115; H01S 3/06791; G02F 1/35
USPC .............................. 385/12, 13, 16, 122–128
See application file for complete search history.

(56) References Cited

FOREIGN PATENT DOCUMENTS

| | | | |
|---|---|---|---|
| CN | 103472001 | A | 12/2013 |
| CN | 105675543 | A | 6/2016 |
| CN | 106770022 | A | 5/2017 |

OTHER PUBLICATIONS

Internation Search Report of PCT/CN2016/112386, dated Sep. 28, 2017.

Linslal, C. L. et al., "Analysis and modeling of an optical fiber loop resonator and an evanescent field absorption sensor for the application for chemical detection", Sensors and Actuators A: Physical, Feb. 7, 2013, pp. 160-168, vol. 194.

* cited by examiner

APPARATUS AND METHOD FOR MEASURING CONCENTRATION OF POLLUTANTS IN WATER

CROSS-REFERENCE TO RELATED APPLICATIONS

This application is a continuation of International Patent Application No. PCT/CN2016/112386 with a filing date of Dec. 27, 2016, designating the United States, now pending. The content of the aforementioned applications, including any intervening amendments thereto, are incorporated herein by reference.

TECHNICAL FIELD

The present disclosure belongs to the technical field of treating pollutants in water, and particularly relates to an apparatus and a method for measuring a concentration of pollutants in water.

BACKGROUND OF THE PRESENT INVENTION

Water resources are important environmental resources for human survival and development. The pollution of the environmental water quality will lead to the chain destruction of an ecological environment system, and ultimately has a serious impact on human daily life and social development. Therefore, protecting a water resource environment has become a globalization problem to which countries all over the world pay attention and attach great importance. China's per capita water resources are in short supply. With the rapid economic development in China and the acceleration of the urbanization process, the pollution of waste water in industries with high energy consumption, high water consumption and high pollution remains high, household waste water in towns is seriously polluted, and surface runoff pollution is even harder to control. Water pollution directly or indirectly affects people's health and life. According to a survey report from the World Health Organization, more than 70% of diseases in developing countries are related to the water pollution. Therefore, the destruction of a water resource environment has become a serious constraint to the sustainable development of the human society and economics in China, and has been highly valued in China. A water quality monitoring instrument is essential equipment for providing a timely, accurate and comprehensive scientific basis for monitoring and treating the water pollution, is an important prerequisite and basis for formulating practical and feasible pollution prevention and control planning and water resource environment protection, and is of paramount importance for safety monitoring and protection of the water resource environment.

At present, the water quality is mainly detected by adopting an ultraviolet-visible spectroscopy technology at home and abroad. The spectroscopy technology needs to realize spectrum scanning by an integrated circuit as a hardware foundation, and application of a stoichiometric method as an algorithm basis. Therefore, water quality analysis instruments currently on the market are often high in cost and complicated to operate.

SUMMARY OF PRESENT INVENTION

The present disclosure provides an apparatus and a method for measuring a concentration of pollutants in water, aiming at solving problems of high cost of measuring the concentration of the pollutants in the water and complicated operation.

In order to solve the above technical problems, the present disclosure provides an apparatus for measuring a concentration of pollutants in water the apparatus includes a passive Q-switched fiber laser, an evanescent field fiber and a spectrum apparatus; the evanescent field fiber is disposed in a laser resonant cavity of the passive Q-switched fiber laser, and the passive Q-switched fiber laser is connected with the spectrum apparatus; the passive Q-switched fiber laser is configured to output an evanescent wave to a to-be-tested water sample after emitting a Q-switched pulse laser signal and transmitting it via an evanescent field fiber, the passive Q-switched fiber laser is further configured to: based on an evanescent wave change caused by an absorption effect of the pollutants in the to-be-tested water sample to the evanescent wave and an output repetition frequency change of the passive Q-switched fiber laser due to the evanescent wave change, output an output repetition frequency result of the passive Q-switched fiber laser, and the spectrum apparatus is configured to display the output repetition frequency result of the passive Q-switched fiber laser.

Further, the spectrum apparatus is further configured to: based on a mapping relationship between a preset output repetition frequency of the passive Q-switched fiber laser and the concentration of the pollutants in the water as well as the output repetition frequency result of the passive Q-switched fiber laser, determine the concentration of the pollutants in the to-be-tested water sample to obtain a measurement result, and display the measurement result.

Further, a cavity structure of the passive Q-switched fiber laser is any one of a ring cavity structure or a linear cavity structure.

The present disclosure further provides a method for measuring a concentration of pollutants in water, wherein an evanescent field fiber is disposed in a laser resonant cavity of a passive Q-switched fiber laser, the method includes: outputting an evanescent wave to a to-be-tested water sample after emitting a Q-switched pulse laser signal and transmitting it via an evanescent field fiber; outputting an output repetition frequency result of the passive Q-switched fiber laser to a spectrum apparatus, based on an evanescent wave change caused by an absorption effect of the pollutants in the to-be-tested water sample to the evanescent wave and an output repetition frequency change of the passive Q-switched fiber laser due to the evanescent wave change; and displaying the output repetition frequency result of the passive Q-switched fiber laser by the spectrum apparatus.

Further, the spectrum apparatus determines the concentration of the pollutants in the to-be-tested water sample to obtain a measurement result based on a mapping relationship between a preset output repetition frequency of the passive Q-switched fiber laser and the concentration of the pollutants in the water as well as the output repetition frequency result of the passive Q-switched fiber laser, and displays the measurement result.

Further, a cavity structure of the passive Q-switched fiber laser is any one of a ring cavity structure or a linear cavity structure.

Compared with the prior art, the present disclosure has the following beneficial effects:

The passive Q-switched fiber laser outputs the evanescent wave to the to-be-tested water sample after emitting the Q-switched pulse laser signal and transmitting it via the evanescent field fiber, and based on the evanescent wave change caused by the absorption effect of the pollutants in the to-be-tested water sample to the evanescent wave and the output repetition frequency change of the passive Q-switched fiber laser due to the evanescent wave change, outputs the output repetition frequency result of the passive Q-switched fiber laser. The method provided by the present disclosure determines the concentration of the pollutants in the water according to the output repetition frequency result of the passive Q-switched fiber laser. The method is simple; and the apparatus based on the method is simple in structure and low in cost.

DETAILED DESCRIPTION OF PREFERRED EMBODIMENTS

In order to make objects, technical solution and advantages of the present disclosure more clear, the present disclosure will be further described in detail with reference to accompanying drawings and embodiments below. It should be understood that the embodiments described here are only for explaining the present disclosure, and not intended as limiting the present disclosure.

Figure 1:
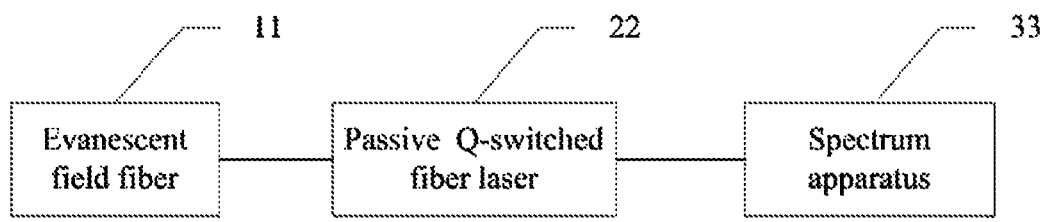
FIG. 1 is a schematic diagram of an apparatus for measuring a concentration of pollutants in water according to a first embodiment of the present disclosure.
Figure 2:
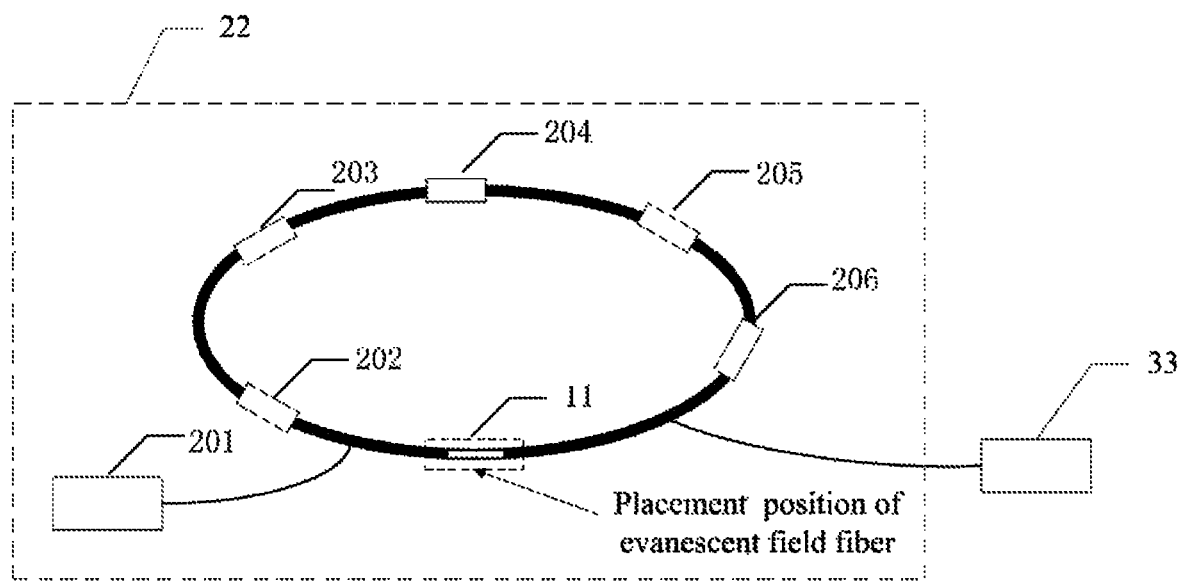
FIG. 2 is a schematic structural diagram of an apparatus for measuring a concentration of pollutants in water according to a first embodiment of the present disclosure.

As a first embodiment of the present disclosure, as shown in FIG. 1 or FIG. 2, the present disclosure provides an apparatus for measuring a concentration of pollutants in water, which includes an evanescent field fiber 11, a passive Q-switched fiber laser 22 and a spectrum apparatus 33.

The evanescent field fiber 11 is disposed in a laser resonant cavity of the passive Q-switched fiber laser 22, and the passive Q-switched fiber laser 22 is connected with the spectrum apparatus 33.

The passive Q-switched fiber laser 22 is configured to output an evanescent wave to a to-be-tested water sample after emitting a Q-switched pulse laser signal and transmitting it via an evanescent field fiber 11.

The passive Q-switched fiber laser 22 is further configured to: based on an evanescent wave change caused by an absorption effect of the pollutants in the to-be-tested water sample to the evanescent wave and an output repetition frequency change of the passive Q-switched fiber laser due to the evanescent wave change, output an output repetition frequency result of the passive Q-switched fiber laser 22.

The spectrum apparatus 33 is configured to display the output repetition frequency result of the passive Q-switched fiber laser 22.

Further, the spectrum apparatus 33 is further configured to: based on a mapping relationship between a preset output repetition frequency of the passive Q-switched fiber laser and the concentration of the pollutants in the water as well as the output repetition frequency result of the passive Q-switched fiber laser, determine the concentration of the pollutants in the to-be-tested water sample to obtain a measurement result, and display the measurement result.

Further, a cavity structure of the passive Q-switched fiber laser 22 is any one of a ring cavity structure or a linear cavity structure. The passive Q-switched fiber laser shown in FIG. 2 is of the ring cavity structure, the spectrum apparatus 33 is connected with the passive Q-switched fiber laser 22, and the evanescent field fiber 11 is disposed in the laser resonant cavity of the passive Q-switched fiber laser 22. In the embodiment of the present disclosure, as shown in FIG. 2, the passive Q-switched fiber laser 22 includes a semiconductor pump laser 201, a wavelength division multiplexer 202, an isolator 203, an erbium doped fiber 204, a saturable absorber 205 and an optical coupler 206, wherein the semiconductor pump laser 201 acts as a pump light source the wavelength division multiplexer 202 is configured to couple a pump light into the resonant cavity; the isolator 203 is configured to prevent optical feedback to enable the laser to run in one direction; the erbium doped fiber 204 acts as a laser gain medium; the saturable absorber 205 acts as a saturable absorber to cause the laser to form a passive Q-switched pulse and the optical coupler 206 is configured to output the laser.

It should be noted that reasons for the evanescent wave change caused by the absorption effect of the pollutants in the to-be-tested water sample to the evanescent wave and the output repetition frequency change of the passive Q-switched fiber laser due to the evanescent wave change are mainly as follows:

When the evanescent wave of light reaches the water, one portion of the evanescent wave will be absorbed by the pollutants in the water. The higher the concentration of the pollutants in the water is, the more the evanescent wave absorbed is. Therefore, the cavity loss of the passive Q-switched fiber laser due to the reduction of the evanescent wave is more, and the change in the cavity loss of the passive Q-switched fiber laser will result in the output repetition frequency change of the passive Q-switched fiber laser. In summary, when the concentration of the pollutants in the to-be-tested water sample changes, the absorption effect of the evanescent wave changes with the change in the concentration of the pollutants in the water, thereby causing the output repetition frequency change of the passive Q-switched fiber laser.

It should be noted that the spectrum apparatus 33 may be a frequency spectrograph or any device capable of displaying a spectrum.

It should be noted that the output repetition frequency of the passive Q-switched fiber laser is generally in the order of above 100 KHz. Since the evanescent field fiber 11 is disposed in the laser resonant cavity of the passive Q-switched fiber laser 22, even if the concentration of the pollutants in the to-be-tested water sample changes very little, the resulting cavity loss of the passive Q-switched fiber laser changes a little. However, due to the oscillation of the resonant cavity, the variation in the cavity loss is amplified, which makes an effect of the cavity loss to the Q-switched laser operation very obvious, and finally enables the output repetition frequency of the passive Q-switched fiber laser 22 in this frequency domain to change, in this way, the measurement is relatively facilitated. When the concentration of the pollutants in the to-be-tested water sample increases, that is, when the loss becomes large, a significant decrease in the Q-switched pulse repetition frequency output by the laser will be caused.

In the embodiment, a single mode fiber is processed to obtain the evanescent field fiber capable of exciting the evanescent field. The following three methods are mainly applied to prepare the evanescent field fiber:

The first one: performing side-polishing on the single mode fiber, wherein a polishing depth reaches 55 microns to 60 microns, which may ensure that the evanescent field is excited;

The second one: tapering the single mode fiber, wherein a tapered waist has a diameter of less than 20 micrometers and greater than 5 micrometers, which may ensure that the evanescent field is excited without being easily damaged, and The third one: performing laser side grooving on the single mode fiber, wherein a groove has a depth of 55 micrometers to 60 micrometers, which may ensure that the evanescent field is excited.

It should be noted that the evanescent field fiber 11 needs to be disposed in the to-be-tested water sample in a measurement process. Therefore, as shown in FIG. 2, a portion, including the evanescent field fiber, of the apparatus is disposed in the to-be-tested water sample in the measurement process.

It should be noted that a range or standard of the mapping relationship between the output repetition frequency of the passive Q-switched fiber laser and the concentration of the pollutants in the water is developed by means of a series of experiments. Firstly, multiple measurements are to be performed on the water sample in which the concentration of the pollutants is known, so as to obtain the range or standard of the output repetition frequency of the passive Q-switched fiber laser at that concentration; secondly, a range or standard of the mapping relationship between the output repetition frequency of the passive Q-switched fiber laser and the concentration of the pollutants in the water is determined according to the range or standard of the output repetition frequency of the passive Q-switched fiber laser; and finally, the obtained standard of the mapping relationship between the output repetition frequency of the passive Q-switched fiber laser and the concentration of the pollutants in the water is recorded into the spectrum apparatus, so that the apparatus for measuring the concentration of the pollutants in the water according to the present disclosure can have an accurate measurement basis.

In addition, the measurement result displayed by the spectrum apparatus 33 may be the output repetition frequency of the passive Q-switched fiber laser 22; or may be the output repetition frequency of the passive Q-switched fiber laser 22, and the output repetition frequency of the passive Q-switched fiber laser at the pre-recorded concentration most similar to it, thereby making a comparison between the two, which is convenient for a user to determine; or may be the concentration, which is obtained after the determination, of the pollutants in the to-be-tested water sample, so that the user can obtain an intuitive measurement result; and the test result can also be any combination of the foregoing cases and the like.

In summary, the method adopted by the apparatus provided by the first embodiment of the present disclosure establishes a correspondence relationship with a variable quantity of the concentration of the pollutants in a water solution and a variable quantity of the repetition frequency in the frequency domain of the passive Q-switched fiber laser by the evanescent wave fiber by utilizing a response of the Q-switched fiber laser in the frequency domain to the external loss. The method is simple and effective, and the apparatus has the advantages of simple structure, low cost, high stability and long service life, and full fibering of components, is suitable for mass production and industrialized promotion, and can better meet the needs for the market.

Figure 3:
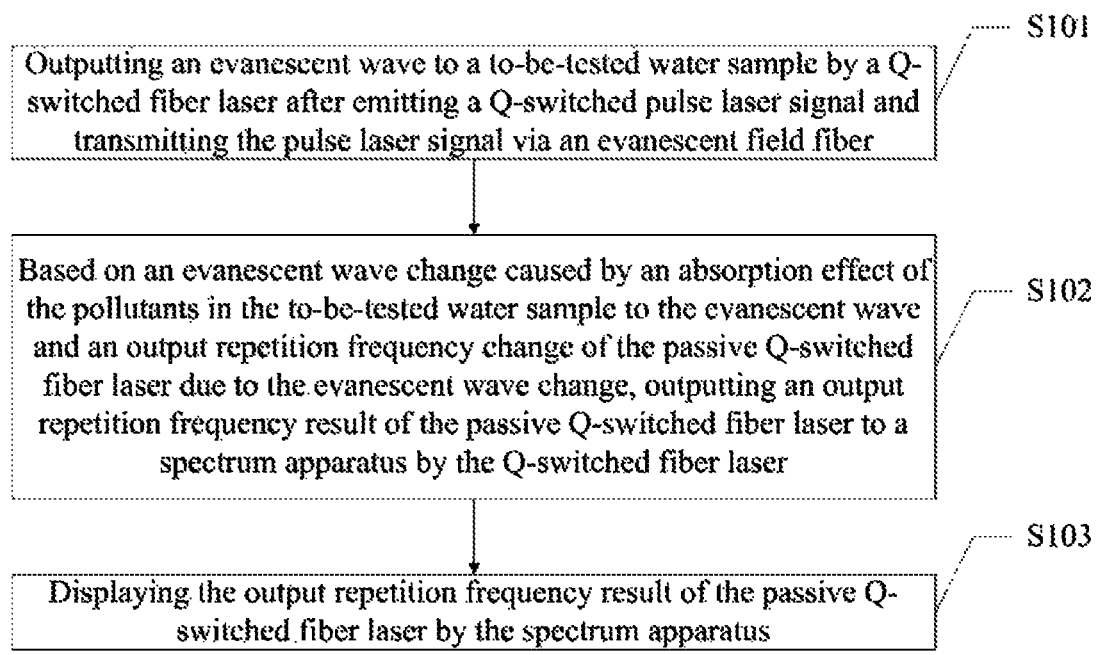
FIG. 3 is a flow diagram of a method for measuring a concentration of pollutants in water according to a second embodiment of the present disclosure.

As a second embodiment of the present disclosure, as shown in FIG. 3, the present disclosure provides a method for measuring a concentration of pollutants in water, wherein an evanescent field fiber is disposed in a laser resonant cavity of a passive Q-switched fiber laser, the method includes:

Step S101, outputting an evanescent wave to a to-be-tested water sample after emitting a Q-switched pulse laser signal and transmitting it via an evanescent field fiber;

Step S102, based on an evanescent wave change caused by an absorption effect of the pollutants in the to-be-tested water sample to the evanescent wave and an output repetition frequency change of the passive Q-switched fiber laser due to the evanescent wave change, outputting an output repetition frequency result of the passive Q-switched fiber laser to a spectrum apparatus; and Step S103, displaying the output repetition frequency result of the passive Q-switched fiber laser by the spectrum apparatus.

It should be noted that reasons for the evanescent wave change caused by the absorption effect of the pollutants in the to-be-tested water sample to the evanescent wave and the output repetition frequency change of the passive Q-switched fiber laser due to the evanescent wave change are mainly as follows:

When the evanescent wave of light reaches the water, one portion of the evanescent wave will be absorbed by the pollutants in the water. The higher the concentration of the pollutants in the water is, the more the evanescent wave absorbed is. Therefore, the cavity loss of the passive Q-switched fiber laser due to the reduction of the evanescent wave is more, and the change in the cavity loss of the passive Q-switched fiber laser will result in the output repetition frequency change of the passive Q-switched fiber laser. In summary, when the concentration of the pollutants in the to-be-tested water sample changes, the absorption effect of the evanescent wave changes with the change in the concentration of the pollutants in the water, thereby causing the output repetition frequency change of the passive Q-switched fiber laser.

It should be noted that the spectrum apparatus may be a frequency spectrograph or any device capable of displaying a spectrum.

It should be noted that the output repetition frequency of the passive Q-switched fiber laser is generally in the order of above 100 KHz. Since the evanescent field fiber is disposed in the laser resonant cavity of the passive Q-switched fiber laser, even if the concentration of the pollutants in the to-be-tested water sample changes very little, the resulting cavity loss of the passive Q-switched fiber laser changes a little. However, due to the oscillation of the resonant cavity, the variation in the cavity loss is amplified, which makes an effect of the cavity loss to the Q-switched laser operation very obvious, and finally enables the output repetition frequency of the passive Q-switched fiber laser in this frequency domain to change, in this way, the measurement is relatively facilitated. When the concentration of the pollutants in the to-be-tested water sample increases, that is, when the loss becomes large, a significant decrease in the Q-switched pulse repetition frequency output by the laser will be caused. In this embodiment, a single mode fiber is processed to obtain the evanescent field fiber capable of exciting the evanescent field. The following three methods are mainly applied to prepare the evanescent field fiber:

The first one: performing side-polishing on the single mode fiber, wherein a polishing depth reaches 55 microns to 60 microns, which may ensure that the evanescent field is excited;

The second one: tapering the single mode fiber, wherein a tapered waist has a diameter of less than 20 micrometers and greater than 5 micrometers, which may ensure that the evanescent field is excited without being easily damaged and The third one: performing laser side grooving on the single mode fiber, wherein a groove has a depth of 55 micrometers to 60 micrometers, which may ensure that the evanescent field is excited.

It should be noted that the evanescent field fiber needs to be disposed in the to-be-tested water sample in a measurement process. Therefore, a portion, including the evanescent field fiber, of the apparatus is disposed in the to-be-tested water sample in the measurement process.

It should be noted that a range or standard of the mapping relationship between the output repetition frequency of the passive Q-switched fiber laser and the concentration of the pollutants in the water is developed by means of a series of experiments. Firstly, multiple measurements are to be performed on the water sample in which the concentration of the pollutants is known, so as to obtain the range or standard of the output repetition frequency of the passive Q-switched fiber laser at that concentration; secondly, a range or standard of the mapping relationship between the output repetition frequency of the passive Q-switched fiber laser and the concentration of the pollutants in the water is determined according to the range or standard of the output repetition frequency of the passive Q-switched fiber laser, and finally, the obtained standard of the mapping relationship between the output repetition frequency of the passive Q-switched fiber laser and the concentration of the pollutants in the water is recorded into the spectrum apparatus, so that the apparatus for measuring the concentration of the pollutants in the water according to the present disclosure can have an accurate measurement basis.

In summary, the method provided by the second embodiment of the present disclosure is simple.

Figure 4:
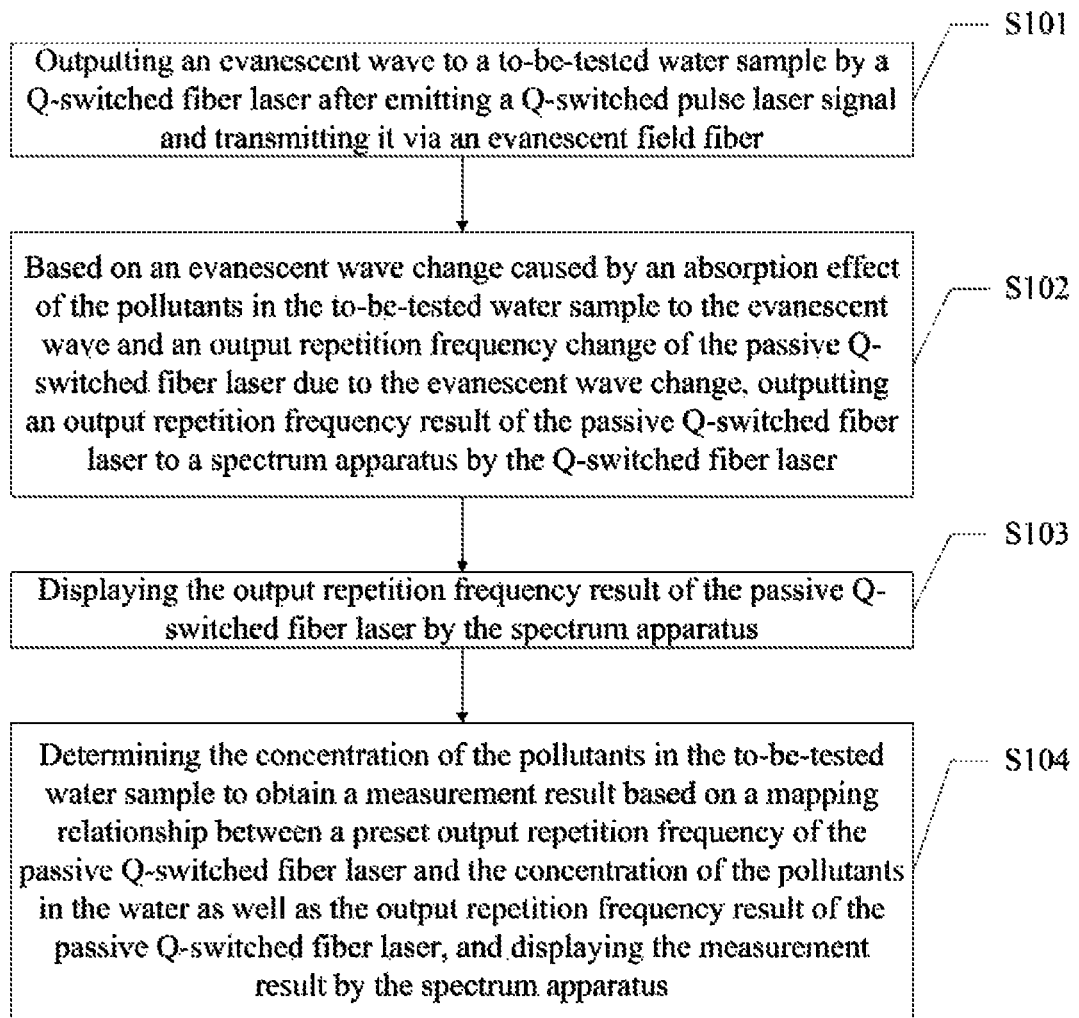
FIG. 4 is a flow diagram of a method for measuring a concentration of pollutants in water according to a third embodiment of the present disclosure.

As a third embodiment of the present disclosure, as shown in FIG. 4, the present disclosure provides a method for measuring a concentration of pollutants in water, wherein an evanescent field fiber is disposed in a laser resonant cavity of a passive Q-switched fiber laser, the method includes:

Step S101, outputting an evanescent wave to a to-be-tested water sample after emitting a Q-switched pulse laser signal and transmitting it via an evanescent field fiber; and Step S102, based on an evanescent wave change caused by an absorption effect of the pollutants in the to-be-tested water sample to the evanescent wave and an output repetition frequency change of the passive Q-switched fiber laser due to the evanescent wave change, outputting an output repetition frequency result of the passive Q-switched fiber laser to a spectrum apparatus;

Step S103, displaying an output repetition frequency result of the passive Q-switched fiber laser by the spectrum apparatus; and Step S104, determining the concentration of the pollutants in the to-be-tested water sample to obtain a measurement result based on a mapping relationship between a preset output repetition frequency of the passive Q-switched fiber laser and the concentration of the pollutants in the water as well as the output repetition frequency result of the passive Q-switched fiber laser, and displaying the measurement result by the spectrum apparatus.

Further, a cavity structure of the passive Q-switched fiber laser is any one of a ring cavity structure or a linear cavity structure.

It should be noted that reasons for the evanescent wave change caused by the absorption effect of the pollutants in the to-be-tested water sample to the evanescent wave and the output repetition frequency change of the passive Q-switched fiber laser due to the evanescent wave change are mainly as follows:

When the evanescent wave of light reaches the water, one portion of the evanescent wave will be absorbed by the pollutants in the water. The higher the concentration of the pollutants in the water is, the more the evanescent wave absorbed is. Therefore, the cavity loss of the passive Q-switched fiber laser due to the reduction of the evanescent wave is more, and the change in the cavity loss of the passive Q-switched fiber laser will result in the output repetition frequency change of the passive Q-switched fiber laser. In summary, when the concentration of the pollutants in the to-be-tested water sample changes, the absorption effect of the evanescent wave changes with the change in the concentration of the pollutants in the water, thereby causing the output repetition frequency change of the passive Q-switched fiber laser.

It should be noted that the spectrum apparatus may be a frequency spectrograph or any device capable of displaying a spectrum.

It should be noted that the output repetition frequency of the passive Q-switched fiber laser is generally in the order of above 100 KHz. Since the evanescent field fiber is disposed in the laser resonant cavity of the passive Q-switched fiber laser, even if the concentration of the pollutants in the to-be-tested water sample changes very little, the resulting cavity loss of the passive Q-switched fiber laser changes a little. However, due to the oscillation of the resonant cavity, the variation in the cavity loss is amplified, which makes an effect of the cavity loss to the Q-switched laser operation very obvious, and finally enables the output repetition frequency of the passive Q-switched fiber laser in this frequency domain to change, in this way, the measurement is relatively facilitated. When the concentration of the pollutants in the to-be-tested water sample increases, that is, when the loss becomes large, a significant decrease in the Q-switched pulse repetition frequency output by the laser will be caused.

In the embodiment, a single mode fiber is processed to obtain the evanescent field fiber capable of exciting the evanescent field. The following three methods are mainly applied to prepare the evanescent field fiber:

The first one: performing side-polishing on the single mode fiber, w herein a polishing depth reaches 55 microns to 60 microns, which may ensure that the evanescent field is excited;

The second one: tapering the single mode fiber, wherein a tapered waist has a diameter of less than 20 micrometers and greater than 5 micrometers, which may ensure that the evanescent field is excited without being easily damaged; and The third one: performing laser side grooving on the single mode fiber, wherein a groove has a depth of 55 micrometers to 60 micrometers, which may ensure that the evanescent field is excited.

It should be noted that the evanescent field fiber needs to be disposed in the to-be-tested water sample in a measurement process. Therefore, a portion, including the evanescent field fiber, of the apparatus is disposed in the to-be-tested water sample in the measurement process.

It should be noted that a range or standard of the mapping relationship between the output repetition frequency of the passive Q-switched fiber laser and the concentration of the pollutants in the water is developed by means of a series of experiments. Firstly, multiple measurements are to be performed on the water sample in which the concentration of the pollutants is known, so as to obtain the range or standard of the output repetition frequency of the passive Q-switched fiber laser at that concentration; secondly, a range or standard of the mapping relationship between the output repetition frequency of the passive Q-switched fiber laser and the concentration of the pollutants in the water is determined according to the range or standard of the output repetition frequency of the passive Q-switched fiber laser; and finally, the obtained standard of the mapping relationship between the output repetition frequency of the passive Q-switched fiber laser and the concentration of the pollutants in the water is recorded into the spectrum apparatus, so that the apparatus for measuring the concentration of the pollutants in the water according to the present disclosure can have an accurate measurement basis.

In addition, the measurement result displayed by the spectrum apparatus may be the output repetition frequency of the passive Q-switched fiber laser; or may be the output repetition frequency of the passive Q-switched fiber laser, and the output repetition frequency of the passive (Q-switched fiber laser at the pre-recorded concentration most similar to it, thereby making a comparison between the two, which is convenient for a user to determine; or may be the concentration, which is obtained after the determination, of the pollutants in the to-be-tested water sample, so that the user can obtain an intuitive measurement result; and the test result can also be any combination of the foregoing cases and the like.

In summary, the method provided by the third embodiment of the present disclosure determines the concentration of the pollutants in water according to the output repetition frequency result of the passive Q-switched fiber laser, and the method is simple and effective.

The above is only preferred embodiments, of the present disclosure, and is not intended as limiting the present disclosure. Any modifications, equivalent substitutions and improvements made within the spirit and principles of the present disclosure should be included in the scope of the present disclosure.

We claim:

1. An apparatus for measuring a concentration of pollutants in water, comprising a passive Q-switched fiber laser, an evanescent field fiber and a spectrum apparatus;
   wherein the evanescent field fiber is disposed in a laser resonant cavity of the passive Q-switched fiber laser, and the passive Q-switched fiber laser is connected with the spectrum apparatus;
   the passive Q-switched fiber laser is configured to output an evanescent wave to a to-be-tested water sample after emitting a Q-switched pulse laser signal and transmitting the Q-switched pulse laser signal via the evanescent field fiber;
   the passive Q-switched fiber laser is further configured to output an output repetition frequency result of the passive Q-switched fiber laser based on an evanescent wave change caused by an absorption effect of the pollutants in the to-be-tested water sample to the evanescent wave and an output repetition frequency change of the passive Q-switched fiber laser due to the evanescent wave change; and
   the spectrum apparatus is configured to display the output repetition frequency result of the passive Q-switched fiber laser.

2. The apparatus according to claim 1, wherein the spectrum apparatus is further configured to determine the concentration of the pollutants in the to-be-tested water sample to obtain a measurement result based on a mapping relationship between a preset output repetition frequency of the passive Q-switched fiber laser and the concentration of the pollutants in the water as well as the output repetition frequency result of the passive Q-switched fiber laser, and to display the measurement result.

3. The apparatus according to claim 1, wherein a cavity structure of the passive Q-switched fiber laser is any one of a ring cavity structure or a linear cavity structure.

4. A method for measuring a concentration of pollutants in water, wherein an evanescent field fiber is disposed in a laser resonant cavity of a passive Q-switched fiber laser, the method comprises:
   outputting an evanescent wave to a to-be-tested water sample after emitting a Q-switched pulse laser signal and transmitting the Q-switched pulse laser signal via the evanescent field fiber; and
   based on an evanescent wave change caused by an absorption effect of the pollutants in the to-be-tested water sample to the evanescent wave and an output repetition frequency change of the passive Q-switched fiber laser due to the evanescent wave change, outputting an output repetition frequency result of the passive Q-switched fiber laser to a spectrum apparatus; and
   displaying the output repetition frequency result of the passive Q-switched fiber laser by the spectrum apparatus.

5. The method according to claim 4, further comprising:
   determining the concentration of the pollutants in the to-be-tested water sample to obtain a measurement result based on a mapping relationship between a preset output repetition frequency of the passive Q-switched fiber laser and the concentration of the pollutants in the water as well as the output repetition frequency result of the passive Q-switched fiber laser, and displaying the measurement result by the spectrum apparatus.

6. The method according to claim 4, wherein a cavity structure of the passive Q-switched fiber laser is any one of a ring cavity structure or a linear cavity structure.

* * * * *